(12) United States Patent
Vad

(10) Patent No.: US 9,675,481 B2
(45) Date of Patent: Jun. 13, 2017

(54) HYBRID BALLOON-EXPANDABLE/SELF-EXPANDING PROSTHESIS FOR DEPLOYMENT IN A BODY VESSEL AND METHOD OF MAKING

(71) Applicant: Cook Medical Technologies LLC, Bloomington, IN (US)

(72) Inventor: Siddharth Vad, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 191 days.

(21) Appl. No.: 14/520,796

(22) Filed: Oct. 22, 2014

(65) Prior Publication Data

US 2015/0034217 A1    Feb. 5, 2015

Related U.S. Application Data

(62) Division of application No. 13/336,310, filed on Dec. 23, 2011, now Pat. No. 8,894,701.

(51) Int. Cl.
| | | |
|---|---|---|
| *A61F 2/94* | (2013.01) | |
| *A61F 2/89* | (2013.01) | |
| *C22F 1/10* | (2006.01) | |
| *A61F 2/958* | (2013.01) | |
| *A61F 2/82* | (2013.01) | |

(52) U.S. Cl.
CPC .................. *A61F 2/94* (2013.01); *A61F 2/89* (2013.01); *C22F 1/10* (2013.01); *A61F 2/958* (2013.01); *A61F 2002/821* (2013.01); *A61F 2002/825* (2013.01); *A61F 2220/0075* (2013.01); *A61F 2250/0048* (2013.01)

(58) Field of Classification Search
CPC .......... A61F 2002/823; A61F 2002/825; A61F 2/89; A61F 2/94; A61F 2250/0019; A61F 2250/004; A61F 2250/0042; A61F 2250/0048
See application file for complete search history.

(56) References Cited

U.S. PATENT DOCUMENTS

| | | |
|---|---|---|
| 4,484,955 A | 11/1984 | Hochstein |
| 6,485,507 B1 | 11/2002 | Walak et al. |

(Continued)

FOREIGN PATENT DOCUMENTS

| | | |
|---|---|---|
| CA | 2468670 A1 | 6/2003 |
| EP | 1 138 280 A2 | 10/2001 |

OTHER PUBLICATIONS

Partial European Search Report dated Jun. 14, 2013, for European Application No. 12275210.8, pp. 1-6.

(Continued)

*Primary Examiner* — Edward Tolan
(74) *Attorney, Agent, or Firm* — Brinks Gilson & Lione

(57) ABSTRACT

A hybrid prosthesis for deployment in a body vessel includes a tubular stent body comprising a wire comprising a shape memory alloy, where the tubular stent body has a self-expanding portion comprising a distal portion of the wire and a balloon-expandable portion comprising a proximal portion of the wire. The shape memory alloy comprises an $A_f$ of less than 37° C. in the self-expanding portion and an $A_s$ of greater than 37° C. in the balloon-expandable portion.

5 Claims, 6 Drawing Sheets

(56) References Cited

U.S. PATENT DOCUMENTS

| | | | |
|---|---|---|---|
| 6,514,285 B1* | 2/2003 | Pinchasik | A61F 2/88 623/1.15 |
| 6,582,461 B1 | 6/2003 | Burmeister et al. | |
| 6,626,937 B1 | 9/2003 | Cox | |
| 6,652,576 B1 | 11/2003 | Stalker | |
| 6,890,350 B1 | 5/2005 | Walak | |
| 6,923,829 B2 | 8/2005 | Boyle et al. | |
| 7,037,327 B2* | 5/2006 | Salmon | A61F 2/90 623/1.11 |
| 7,175,655 B1* | 2/2007 | Molaei | A61F 2/86 623/1.18 |
| 7,632,303 B1 | 12/2009 | Stalker et al. | |
| 2002/0007102 A1 | 1/2002 | Salmon et al. | |
| 2003/0105513 A1* | 6/2003 | Moriuchi | A61F 2/91 623/1.15 |
| 2003/0195609 A1 | 10/2003 | Berenstein et al. | |
| 2005/0004647 A1 | 1/2005 | Bassoe | |
| 2006/0074403 A1 | 4/2006 | Rafiee | |
| 2007/0005126 A1 | 1/2007 | Tischler | |
| 2007/0219618 A1* | 9/2007 | Cully | A61F 2/88 623/1.13 |
| 2007/0293940 A1 | 12/2007 | Schaeffer et al. | |
| 2009/0125095 A1 | 5/2009 | Bui et al. | |
| 2009/0210048 A1* | 8/2009 | Amplatz | A61F 2/07 623/1.13 |
| 2011/0152994 A1* | 6/2011 | Hendriksen | A61F 2/91 623/1.11 |
| 2011/0172762 A1 | 7/2011 | Hartley et al. | |
| 2011/0265908 A1* | 11/2011 | Clerc | A61F 2/90 140/71 R |
| 2012/0029624 A1* | 2/2012 | Dierking | A61F 2/07 623/1.16 |
| 2015/0232975 A1* | 8/2015 | Tofail | C22F 1/10 148/556 |

OTHER PUBLICATIONS

Scurr, R.H. James et al., "Fenestrated Stent-Graft Repair: Which Stent Should Be Used to Secure Target Vessel Fenestrations?," *J of Endovascular Therapy* (2008) pp. 344-348.

Extended European Search Report dated Feb. 16, 2017, for European Application No. 16197983.6, pp. 1-7.

\* cited by examiner

HYBRID BALLOON-EXPANDABLE/SELF-EXPANDING PROSTHESIS FOR DEPLOYMENT IN A BODY VESSEL AND METHOD OF MAKING

RELATED APPLICATIONS

The present patent document is a division of U.S. patent application Ser. No. 13/336,310, filed Dec. 23, 2011, which is hereby incorporated by reference in its entirety.

TECHNICAL FIELD

The present disclosure is related generally to stents and more particularly to stents that have both balloon-expandable and self-expanding portions.

BACKGROUND

Aneurysms occur in blood vessels at sites where, due to age, disease or genetic predisposition of the patient, the strength or resilience of the vessel wall is insufficient to prevent ballooning or stretching of the wall as blood passes through. If the aneurysm is left untreated, the blood vessel wall may expand and rupture, often resulting in death.

Stent grafts may be used to treat aneurysms. A stent graft includes a graft material secured to a cylindrical scaffolding or framework of one or more stents. The stent graft may be introduced into a blood vessel percutaneously and deployed to span the aneurysmal sac. The stent(s) provide rigidity and structure to hold the graft material open in a tubular configuration as well as the outward radial force needed to create a seal between the graft material and a healthy portion of the vessel wall. Blood flowing through the vessel can be channeled through the hollow interior of the stent graft to reduce or eliminate the stress on the vessel wall at the location of the aneurysmal sac.

Aneurysms occurring in the aorta, the largest artery in the human body, may occur in the chest (thoracic aortic aneurysm) or in the abdomen (abdominal aortic aneurysm). With the advent of fenestration, branch and chimney techniques, it has been possible to treat patients with short angulated necks, aneurysmal extension into either internal iliac arteries or complex aneurysmal involvement of the juxtarenal, paravisceral, and thoracoabdominal aorta using minimally invasive techniques (e.g., EVAR or f-EVAR). The techniques may involve the use of a modular stent graft having (a) a main body stent graft to cover and achieve patency in the aneurysmatic aorta and (b) a side arm stent graft to reach target vessels (e.g., celiac, SMA, renal arteries, internal iliacs, great vessels of the aortic arch). The target vessels exhibit varying levels of tortuousity, with acute tortuousity shown by great vessels of the aortic arch and iliac branches.

The stent used to bridge the gap between the main graft and the target vessel has to endure branch vessel motion relative to the aorta, arterial motion, and motion due to respiration and physical movements which may cause it to crush or collapse at the interface. This warrants the design of more radially stiff bridging stents without sacrificing the plasticity needed to deform and anchor such stents in place. However, the bridging stents also encounter branch vessel tortuousity, which makes it necessary for the stents to be flexible. Flexibility and radial stiffness are antipodal and it is generally believed that radial stiffness must be sacrificed to achieve flexibility and vice versa.

BRIEF SUMMARY

A hybrid balloon-expandable/self-expanding stent fabricated from a cannula or wire is described. The hybrid prosthesis may offer a previously unattainable balance of flexibility and stiffness from a monolithic stent body. Also described is an endoluminal hybrid prosthesis system and a method of making a hybrid prosthesis.

According to one embodiment, the hybrid prosthesis includes a tubular stent body comprising a wire comprising a shape memory alloy, where the tubular stent body has a self-expanding portion comprising a distal portion of the wire and a balloon-expandable portion comprising a proximal portion of the wire. The shape memory alloy comprises an $A_f$ of less than 37° C. in the self-expanding portion and an $A_s$ of greater than 37° C. in the balloon-expandable portion.

According to another embodiment, the hybrid prosthesis includes a tubular stent body comprising a wire comprising a shape memory alloy, where the tubular stent body has a self-expanding portion comprising a distal portion of the wire and a balloon-expandable portion comprising a proximal portion of the wire. The distal portion has a helical configuration comprising bent wire first portions alternating with straight wire first portions in a helical zigzag pattern about a longitudinal axis of the stent body, and the proximal portion has a ring-like configuration including one or more rings centered about a longitudinal axis of the stent body, each of the one or more rings including bent wire second portions alternating with straight wire second portions in a circumferential zigzag pattern about the longitudinal axis.

The endoluminal hybrid prosthesis system comprises: a main body prosthesis for deployment in a main vessel body lumen, the main body prosthesis comprising a graft material attached to a tubular main stent body so as to form a tubular primary lumen for fluid flow therethrough, where the graft material comprises a fenestration; and a side arm prosthesis for deployment in a side vessel body lumen and attached to the main body prosthesis at the fenestration, where the side arm prosthesis comprises a graft material attached to a tubular secondary stent body so as to form a tubular secondary lumen for fluid flow therethrough. The tubular primary lumen and the tubular secondary lumen are in fluid communication. The tubular secondary stent body comprises a wire comprising a shape memory alloy, the tubular secondary stent body having a self-expanding portion comprising a distal portion of the wire and a balloon-expandable portion comprising a proximal portion of the wire, wherein the shape memory alloy comprises an $A_f$ of less than 37° C. in the self-expanding portion and an $A_s$ of greater than 37° C. in the balloon-expandable portion.

The method comprises: loading a proximal portion of a stent body comprising a shape memory alloy into a first hollow mandrel, the shape memory alloy having values of $A_s$ and $A_f$ below body temperature; loading a distal portion of the stent body comprising the shape memory alloy over a second hollow mandrel, the second hollow mandrel comprising one or more throughholes in a wall thereof for passage of a cooling fluid; heating the proximal portion of the stent body to a temperature in the range of from about 300° C. to about 550° C.; exposing the distal portion of the stent body to a cooling fluid during the heating; and increasing the values of $A_s$ and $A_f$ in the proximal portion of the stent body to greater than body temperature while the values of $A_s$ and $A_f$ in the distal portion of the stent body remain below body temperature, thereby forming a hybrid prosthesis including a balloon expandable proximal portion and a self-expanding distal portion.

DETAILED DESCRIPTION

Figure 1A:
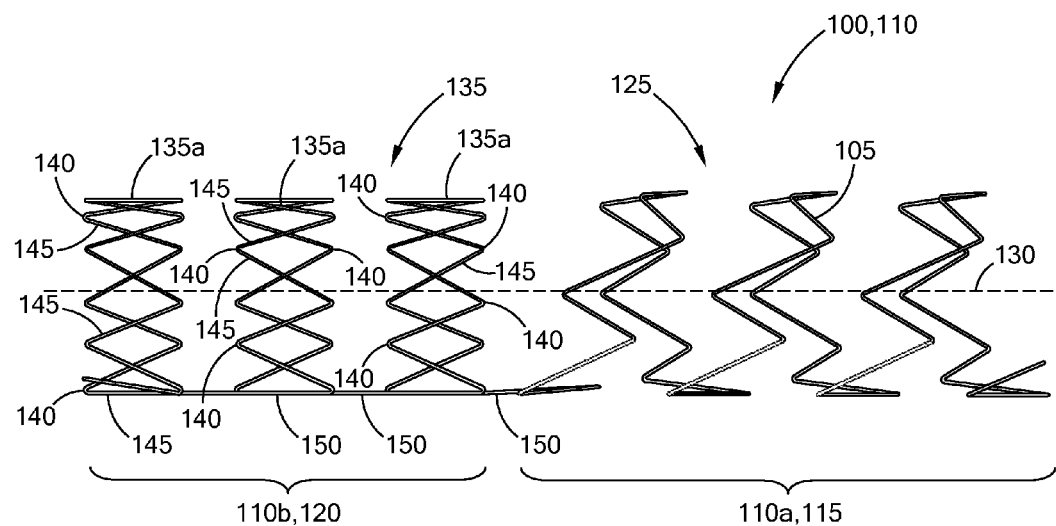
FIG. 1A is a schematic of an exemplary hybrid prosthesis including balloon-expandable and self-expanding portions.

As used in the following specification and the appended claims, the following terms will have the meanings ascribed below:

The term "distal" refers to the portion of an intraluminal device or part of the aorta that is farther away from the heart in the direction of blood flow through the aorta.

The term "proximal" refers to the portion of an intraluminal device or part of the aorta that is nearer to the heart.

Martensite start temperature ($M_s$) is the temperature at which a phase transformation to martensite begins upon cooling for a shape memory material exhibiting a martensitic phase transformation.

Martensite finish temperature ($M_f$) is the temperature at which the phase transformation to martensite concludes upon cooling.

Austenite start temperature ($A_s$) is the temperature at which a phase transformation to austenite begins upon heating for a shape memory material exhibiting an austenitic phase transformation.

Austenite finish temperature ($A_f$) is the temperature at which the phase transformation to austenite concludes upon heating.

R'-phase start temperature ($R'_s$) is the temperature at which a phase transformation to R-phase begins upon heating for shape memory material exhibiting an R-phase transformation.

R'-phase finish temperature ($R'_f$) is the temperature at which the phase transformation to R-phase concludes upon heating.

R-phase start temperature ($R_s$) is the temperature at which a phase transformation to R-phase begins upon cooling for a shape memory material exhibiting an R-phase transformation.

R-phase finish temperature ($R_f$) is the temperature at which the phase transformation to R-phase concludes upon cooling.

The phrase "austenite transformation temperatures" is used in reference to $A_s$ and $A_f$.

A method has been developed to fabricate a hybrid stent comprising a shape memory alloy that can exhibit two different expansion behaviors at body temperature (37° C.). The technology enables the creation of a balloon-expandable/self-expanding combination prosthesis that is free from any joints or welds. The hybrid stent, which may be made from a single continuous wire or cut from a monolithic cannula, can be used for endovascular applications to treat aneurysms. For example, the hybrid stent may be employed as a bridging stent for fenestrated, chimney or branched stent grafts. The hybrid stent also holds a promise for use in transjugular intrahepatic portosystemic shunt (TIPS) procedures.

The method includes controlling the austenite transformation temperatures ($A_s$, $A_f$) of a shape memory alloy such as Nitinol in different portions of a stent. When $A_s$ and $A_f$ have values below body temperature, the shape memory alloy is fully austenitic at body temperature and superelastic deployment of a stent (or stent portion) is possible. When $A_s$ and $A_f$ have values above body temperature, the shape memory alloy remains martensitic at body temperature and plastic deformation (e.g., balloon expansion) may be exploited to deploy the stent (or stent portion).

Referring to FIG. 1A, the hybrid prosthesis 100 includes a tubular stent body 110 comprising a wire 105 comprising a shape memory alloy. The tubular stent body 110 has a self-expanding portion 110a comprising a distal portion of the wire 105 and a balloon-expandable portion 110b comprising a proximal portion 120 of the wire 105. The shape memory alloy comprises an $A_f$ of less than 37° C. in the self-expanding portion 110a and an $A_s$ of greater than 37° C. in the balloon-expandable portion 110b. To achieve different values of the austenite transformation temperatures in the balloon-expandable and self-expanding portions 110b, 110a of the stent body 110, the proximal portion 120 of the wire 105 undergoes a thermal process that is different from the distal portion 115 of the wire 105, as discussed in detail below.

The self-expanding portion 110a of the stent body 110 is designed to be flexible and kink resistant, while the balloon-expandable portion 110b of the stent body 110 is intended to provide higher stiffness. The proximal portion 120 of the wire 105 may have a ring-like configuration 135 that includes one or more rings 135a centered about the longitudinal axis 130 of the stent body 110, where each ring 135a comprises bent wire portions 140 alternating with straight wire portions 145 in a circumferential zigzag pattern about the longitudinal axis 130. The term "circumferential" generally refers to a pathway defined by the circumference of the stent body 110, which has a generally cylindrical shape, as shown in FIG. 1A. The bent wire portions 140 include alternating peaks and valleys with the straight wire portions 145 inbetween. Such a circumferential zigzag pattern may be found, for example, in the structure of the Zenith® stents made by Cook Medical Technologies LLC (Bloomington, Ind.). The distal portion 115 of the wire 105 may have a helical configuration 125 comprising bent wire portions 155 alternating with straight wire portions 160 in a helical zigzag pattern about the longitudinal axis 130, as illustrated in FIG. 1A. The term "helical" generally refers to a pathway defined by a helix including one or more turns about the longitudinal axis 130 of the stent body 110.

In embodiments in which the proximal portion 120 includes a plurality (two or more) of rings 135a, successive rings 135a may be joined by an interconnecting wire portion 150 so that the balloon-expandable portion 110b of the stent body 110 is formed by a single continuous wire 105 (which also forms the self-expanding portion 110a). It is also contemplated that the balloon-expandable portion 110b may include one or more additional wires having the ring-like configuration and spaced longitudinally apart from (and not joined to) the single continuous wire in a proximal direction. Similarly, the self-expanding portion 110a may further comprise one or more additional wires having the helical configuration and spaced longitudinally apart from (and not joined to) the single continuous wire in a distal direction. It is further contemplated that the single continuous wire may include a plurality of wire strands that are twisted, braided, or otherwise assembled together. The wire may also have a core-shell structure formed from two different materials by coextrusion, vapor deposition, or another method. For example, a radiopaque metal such as platinum or gold may form the core, and a nickel-titanium shape memory alloy may form the shell of the core-shell structure.

Figure 1B:
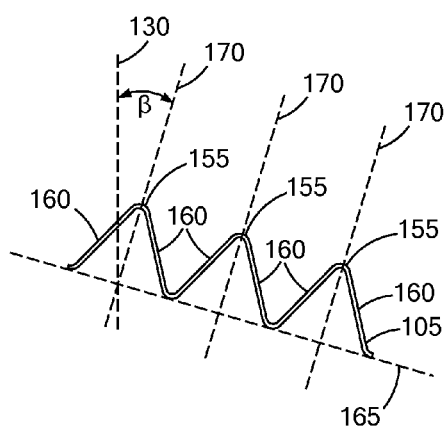
FIG. 1B is a flattened side view schematic of part of the self-expanding portion of the hybrid prosthesis of FIG. 1A, according to a first embodiment.
Figure 1C:
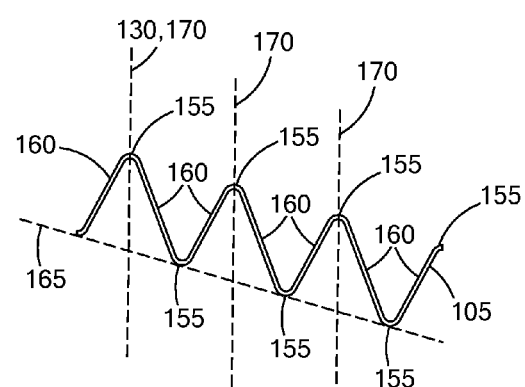
FIG. 1C is a flattened side view schematic of part of the self-expanding portion of the hybrid prosthesis of FIG. 1A, according to a second embodiment.

FIGS. 1B and 1C are flattened side view schematics showing two exemplary embodiments of the helical zigzag pattern of the distal portion 115 of the wire 105 that defines the self-expanding portion 110a of the stent body 110. In the embodiment shown in FIG. 1B, all of the straight wire portions 160 between the bent wire portions 155 (alternating peaks and valleys) have the same length, such that a straight line 170 drawn from a peak 155 to a baseline 165 of the helical configuration 125 defines a nonzero angle β with respect to the longitudinal axis 130 of the stent body 110. In contrast, in the embodiment of FIG. 1C, every other straight portion 160 has the same length. Accordingly, for a given bent wire portion 155, the straight portion 160 on one side of the bent wire portion 155 is shorter than the straight portion 160 on the other side of the bent wire portion 155, such that a straight line 170 drawn from a peak 155 to a baseline 165 of the helical configuration 125 is aligned with the longitudinal axis of the stent body 110. Such a helical zigzag pattern is further described in U.S. Patent Application Publication 2010/0198333, which is hereby incorporated by reference in its entirety.

The stent body may range in (expanded) diameter from about 4 mm to about 12 mm, or more particularly between about 6 mm to about 10 mm. A graft material may be attached to the stent body and define a tubular lumen for fluid flow therethrough.

Figure 2:
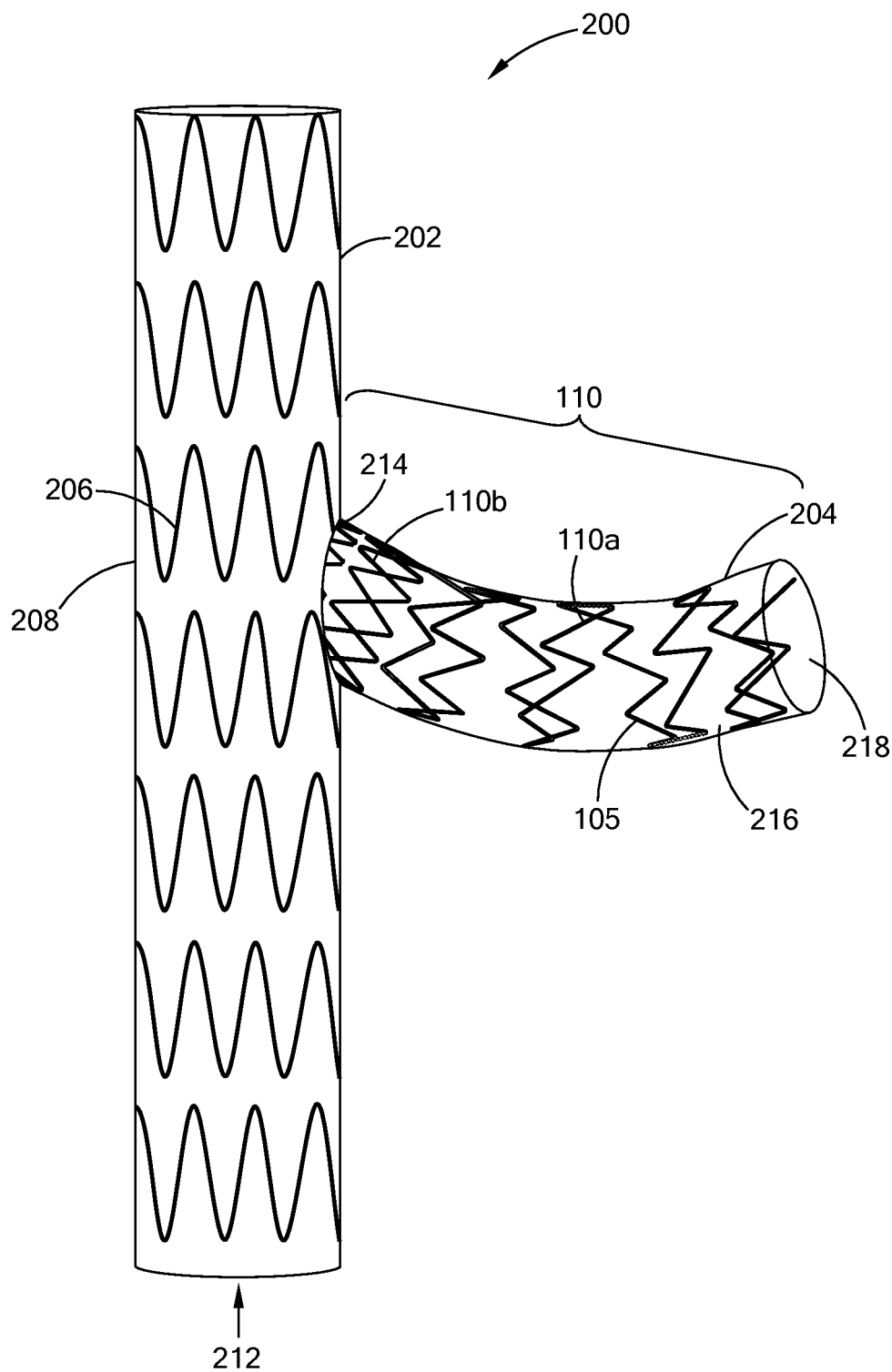
FIG. 2 shows an exemplary hybrid prosthesis system including a main body prosthesis and a side arm (or side branch) prosthesis.

The hybrid prosthesis may be a side arm prosthesis deployable in a branch vessel body lumen. FIG. 2 shows an exemplary endoluminal prosthesis system 200 for a branched body lumen, which includes a main body prosthesis 202 for deployment in a main vessel lumen and a hybrid side arm prosthesis 204 for deployment in a branch vessel lumen.

The main body prosthesis 202 includes a main stent body 206 attached to a graft material 208 which defines a tubular primary lumen 212 for fluid flow therethrough and includes a fenestration 214. The hybrid side arm prosthesis 204, which is attached to the main body prosthesis at the fenestration 214, includes a secondary stent body 110 attached to a graft material 216 that defines a tubular secondary lumen 218 for fluid flow therethrough.

The secondary stent body 110 has self-expanding and balloon-expandable portions 110a, 110b defined by respective distal and proximal portions 115, 120 of a wire 105 comprising a shape memory alloy. The wire 105 has been processed to have different values of $A_s$ and $A_f$ in the proximal and distal portions 120, 115 thereof. Accordingly, the self-expanding portion 110a of the stent body 110 includes an $A_f$ of less than 37° C. and the balloon-expandable portion 110b includes an $A_s$ of greater than 37° C.

The distal portion 115 of the wire 105 that defines the self-expanding portion 110a of the stent body 110 may have a helical configuration 125, as shown in FIG. 1A, and as described previously. The distal portion 115 of the wire 105 may alternatively have other configurations conducive to providing a flexible and kink-resistant portion of the secondary stent body 110.

The proximal portion 120 of the wire 105 that defines the balloon-expandable portion 110b of the stent body 110 may have a ring-like configuration 235 as shown in FIG. 1A and as described previously. Alternatively, the proximal portion 120 of the wire 105 may have other configurations conducive to providing a stiff portion of the secondary stent body 110.

The balloon-expandable portion 110b of the stent body 110 may comprise a flareable end portion for securing the side arm prosthesis 204 to the main body prosthesis 202, as described below in reference to FIG. 4D. The hybrid side arm prosthesis 204 may further include any of the features discussed above with respect to the hybrid prosthesis 100 shown in FIG. 1A.

To fabricate a hybrid prosthesis that has both self-expanding and balloon-expandable portions, distal and proximal portions of the wire comprising the shape memory alloy undergo different thermal processing treatments. As a result, different austenite transformation temperatures are achieved in each portion of the wire.

Prior to the thermal processing treatment, the wire is formed into a stent body of the desired geometry or geometries. The wire used to define the stent body may be laser-cut or otherwise machined out of a tubular cannula, or it may be obtained from a typical wire drawing process. In the latter case, the stent body may be made by winding the wire around a mandrel with a circular cross-section, where the mandrel contains a series of pins that extend radially outward from the mandrel in a predetermined arrangement, depending on the desired stent geometry. The wire may be bent around the pins and around the mandrel to obtain the desired stent geometry (e.g., the helical and/or circumferential zigzag patterns described earlier), followed by a heat setting treatment, as described below. The stent body may also be formed as described in U.S. Patent Application Publication 2010/0198333. As shown in FIGS. 1 and 2, the proximal portion of the stent body may have a different configuration than the distal portion of the stent body. Alternatively, referring to FIGS. 3A-3C, which shows a Cook Medical Zilver stent before and after the thermal processing treatment, the stent body may have a single stent geometry across the proximal and distal portions.

As stated above, once formed, the stent body may undergo a heat setting treatment to impart a remembered shape thereto (e.g., a radially expanded configuration) and to ensure that the stent body is fully austenitic at body temperature prior to the thermal processing treatment. Typically, heat setting is carried out at a temperature between about 350° C. and about 550° C. for a time duration of about 5-60 min. It is desired that the austenite transformation temperatures ($A_s$ and $A_f$) of the stent body are initially less than body temperature (i.e., less than 37° C.), and they may also be less than room temperature (e.g., about 25° C. or less) initially. For example, an initial value of $A_f$ may lie between −15° C. and 25° C.

Figure 3A:
FIGS. 3A-3C show an exemplary stent body in preparation for a thermal processing treatment to phase transformation temperatures.
Figure 3B:

Referring now to FIGS. 3A and 3B, the proximal portion of the stent body having initial austenite transformation temperatures less than 37° C. is loaded into a first hollow mandrel, and the distal portion of the stent body is loaded over a second hollow mandrel, which includes one or more throughholes in a wall thereof for passage of a cooling fluid. The first and second hollow mandrels may be constructed from brass or another thermally conductive material.

Next, the proximal portion of the stent body is heated to a temperature in the range of from about 300° C. to about 550° C., while the distal portion of the stent body is cooled by exposure to a cooling fluid. The cooling fluid may be air, water, liquid nitrogen and/or other coolants, and the fluid may be continuously circulated over the distal portion of the stent body. To heat the proximal portion of the stent body, the first hollow mandrel and the proximal portion of the stent body contained therein may be immersed in a sand bath. The heating may be carried out for a time duration from about 10 minutes to about 180 minutes, and preferably within the temperature range of from about 350° C. to about 450° C.

As a consequence of the thermal processing treatment, the austenite transformation temperatures of the proximal portion of the stent body are raised sufficiently to ensure that the proximal portion does not transform to austenite upon exposure to body temperature. Specifically, $A_s$ and $A_f$ in the proximal portion of the stent body are raised to values greater than 37° C. If the shape memory alloy is a two-stage Nitinol alloy exhibiting an R-phase transformation in addition to martensitic and austenitic transformations, then the R-phase transformation temperatures ($R_s$ and $R_f$) in the proximal portion may also be increased above body temperature. As a result, when used in the body, the proximal portion of the stent body remains martensitic (and thus balloon-expandable).

In contrast, due to the exposure to the cooling fluid while the proximal portion of the stent body is heated, the distal portion of the stent body does not experience an increase in the austenite transformation temperatures. $A_s$ and $A_f$ remain below 37° C. in the distal portion of the stent body, and thus, when used in the body, the distal portion is fully austenitic and thus self-expanding.

Figure 3C:
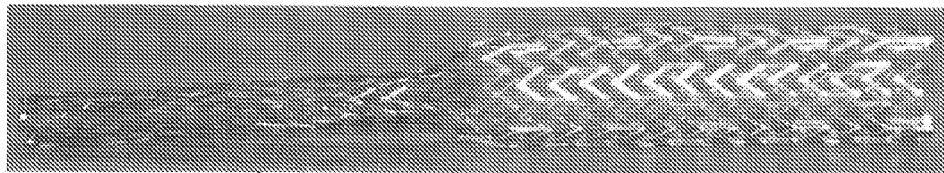

Accordingly, a stent body having a balloon expandable portion and a self-expanding portion is formed, as shown in FIG. 3C.

The change in the austenite transformation temperatures in the proximal portion of the stent body as a consequence of the heating in the sand bath may be understood in view of microstructural changes that occur. When the shape memory alloy is an equiatomic or near-equiatomic nickel-titanium (Ni-Ti) alloy, the temperature increase may cause nickel-rich precipitates to form in the alloy, producing localized shifts in composition and depleting the Ni-Ti alloy matrix of nickel. However, the overall composition of the alloy remains the same. Due to the localized depletion of nickel from the Ni-Ti alloy matrix, the austenite transformation temperatures ($A_s$ and $A_f$) may increase. When heated for sufficient time, the $A_s$ temperature of the proximal portion of the stent body increases above 37° C., ensuring that the Ni-Ti alloy remains martensitic at body temperature. Thus, the portion of the stent constrained inside the first hollow mandrel becomes balloon-expandable. Since only the proximal portion of the stent body experiences the heat treatment due to the highly efficient mandrel and the cooling of the distal portion, the initial austenite transformation temperatures in the distal portion do not change substantially. Accordingly, the distal portion of the stent remains superelastic at body temperature.

Prior to loading the proximal portion of the stent body into the first hollow mandrel, the stent body may be partially compressed. The first hollow mandrel may have an inner diameter slightly larger than an outer diameter of a compressed medical balloon on a balloon catheter, and after fabrication the hybrid prosthesis may be loaded onto the catheter and fully crimped or compressed into a delivery position.

Referring again to FIG. 3A (inset), to allow a smooth transition between the proximal portion of the stent body, which may be compressed within the first hollow mandrel for the heat treatment, and the distal portion of the stent body, which is expanded during the cooling, the first hollow mandrel may include a tapered portion at a distal end thereof, where the tapered portion increases from a constant diameter to a larger diameter in a distal direction. In addition, the second hollow mandrel may have an outer diameter larger than the inner diameter of the first hollow mandrel, and the outer diameter of the second hollow mandrel may also be larger than the outer diameter of the first hollow mandrel. A remaining portion of the first hollow mandrel comprises an untapered portion having the constant diameter along a length of the remaining portion.

In practice, differential scanning calorimetry (DSC) techniques known in the art may be used to determine phase transformation temperatures (e.g., $A_s$, $A_f$) of the shape memory alloy. DSC measurements may be carried out according to the American Society for Testing and Materials (ASTM) standard F2004-05 entitled "Standard Test Method for Transformation Temperature of Nickel-Titanium Alloys by Thermal Analysis," which is hereby incorporated by reference. In the case of a two-stage Nitinol alloy exhibiting an R-phase transformation in addition to martensitic and austenitic phase transformations, the DSC method set forth in U.S. Patent Application Publication 2009/0139614, "Method of Characterizing Phase Transformations in Shape Memory Materials," which is hereby incorporated by reference in its entirety, may be employed to identify the phase transformation temperatures.

Alternatively, methods known as constant load dilatometry and bend and free recovery may be employed to determine the transformation temperatures. Bend and free recovery tests may be carried out in accordance with the ASTM standard F2082-03 entitled "Standard Test Method for Determination of Transformation Temperature of Nickel-Titanium Shape Memory Alloys by Bend and Free Recovery," which is hereby incorporated by reference. Electrical resistivity measurements are also known in the art for determining the phase transformation temperatures of metals and alloys. Such measurements may be carried out by heating and cooling the alloy of interest while recording voltage using a four-probe constant current technique, for example. Using electrical resisitivity measurements, it is possible to characterize phase transformations occurring in the nickel-titanium alloy as a function of applied stress as well as temperature.

As indicated above, the shape memory alloy is advantageously an equiatomic or near-equiatomic nickel-titanium alloy, sometimes referred to as a Nitinol alloy. Such alloys include an atomic ratio of nickel to titanium (at. % Ni:at. % Ti) in the range of from 45:55 to 55:45, where an equiatomic ratio is defined as 50:50 (50 at. % Ni:50 at. % Ti). As known to one of ordinary skill in the art, a nickel-titanium shape memory alloy (which may also be referred to as a nickel-titanium superelastic alloy) undergoes a reversible phase transformation between a martensitic phase and an austenitic phase that allows it to "remember" and return to a previous shape or configuration. For example, compressive strain imparted to a martensitic stent to achieve a low-profile delivery configuration may be substantially recovered during a reverse phase transformation to austenite, such that the stent expands to a "remembered" (e.g., expanded) configuration at a treatment site in a vessel. Typically, recoverable strains of about 8-10% may be obtained from superelastic nickel-titanium alloys. The forward and reverse phase transformations may be driven by a change in stress (superelastic effect) and/or temperature (shape memory effect).

Slightly nickel-rich Nitinol alloys including, for example, about 51 at. % Ni and about 49 at. % Ti are known to be useful for medical devices which are superelastic at body temperature. In particular, alloys including 50.6-50.8 at. % Ni and 49.2-49.4 at.% Ti are considered to be medical grade Nitinol alloys and are suitable for use in the stent body. The nickel-titanium alloy may further include one or more additional alloying elements as substitutional elements for the nickel and/or titanium. In addition, nickel-titanium alloy wire including an inner core of platinum, palladium, or another radiopaque material, may also be employed.

Any of a number of known graft materials, such as biocompatible polymers, may be employed and attached to the primary and/or secondary stent body. The graft material may be attached using methods known in the art, such as by stitching using a monofilament or braided suture material. An entirety or only a portion of the stent body may be covered or by the graft material, which defines the lumen of the stent graft and which may overlie or underlie the stent body.

Figure 4A:
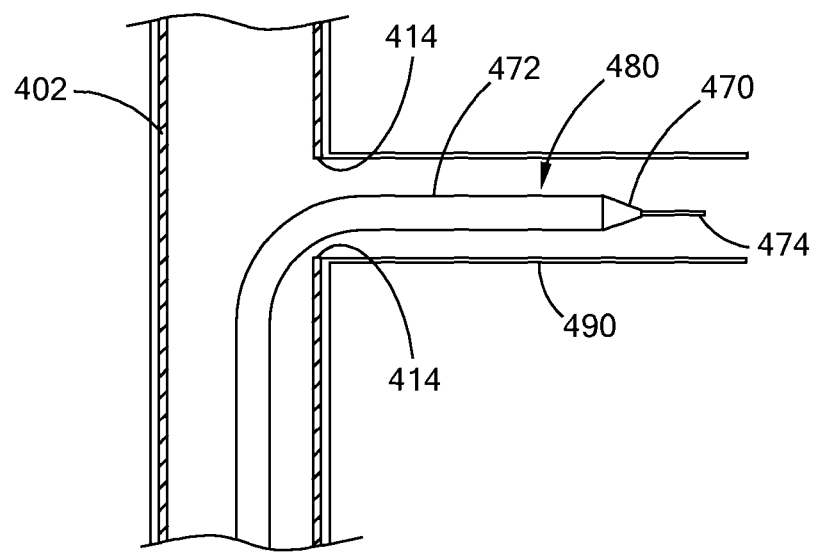
FIGS. 4A-4E show an exemplary deployment procedure for the hybrid prosthesis.

FIGS. 4A-4E illustrate various stages of deployment of an exemplary hybrid branch vessel prosthesis. Referring to FIG. 4A, a main vessel prosthesis 402 is shown already deployed within the main body lumen in a position where a fenestration 414 generally aligns with the opening of a branch vessel. The main vessel prosthesis 402 can be deployed in any manner known in the art, including the method described in PCT Patent Application WO 98/53761, which is hereby incorporated by reference in its entirety. The hybrid branch vessel prosthesis 404 includes a hybrid balloon-expandable/self-expanding stent body and attached graft material, as described previously, in a delivery (compressed) configuration over a balloon catheter 470. A tubular sheath 472 overlies the self-expanding distal portion of the stent body, and a compressed balloon underlies the proximal portion of the stent body. Retraction of the tubular sheath 472 is used to deploy the self-expanding portion of the stent body, and inflation of the balloon is employed to deploy the balloon-expandable portion of the stent body once the hybrid branch vessel prosthesis 404 is properly positioned within the branch vessel. For simplicity of illustration, a straight branch vessel is shown in FIGS. 4A-4E; however, in reality this vessel may be quite tortuous and the hybrid branch vessel prosthesis 404 may therefore undergo flexing and other deformation during insertion and deployment. Details of the deployment are discussed below.

Once the main vessel prosthesis 402 is deployed, a delivery device 480 containing the hybrid branch vessel prosthesis 404 in a delivery configuration may be inserted into an artery via a surgical cut-down, or by percutaneous access techniques that are well known in the art. A guide wire 474 is introduced into the artery and advanced through the lumen of the main vessel prosthesis 402 and distally through the fenestration 414 into the branch vessel 490, as shown in FIG. 4A, until the prosthesis contained in the delivery device 480 is properly positioned in the branch vessel 490. Standard radiographic techniques may be employed to achieve proper positioning by aligning the prosthesis with the fenestration 414. For example, the main vessel prosthesis 402 may comprise a positional indicator (not shown) that generally indicates the fenestration 414. A radiopaque marker, located on the stent, and/or positional indicator located on the delivery device 480, may be coordinated with the fenestration indicator to ensure proper positioning and orientation of the branch vessel prosthesis 404 with respect to the main vessel prosthesis 402. Once the prosthesis 404 is properly positioned, the delivery device 480 is ready for deployment.

Figure 4B:
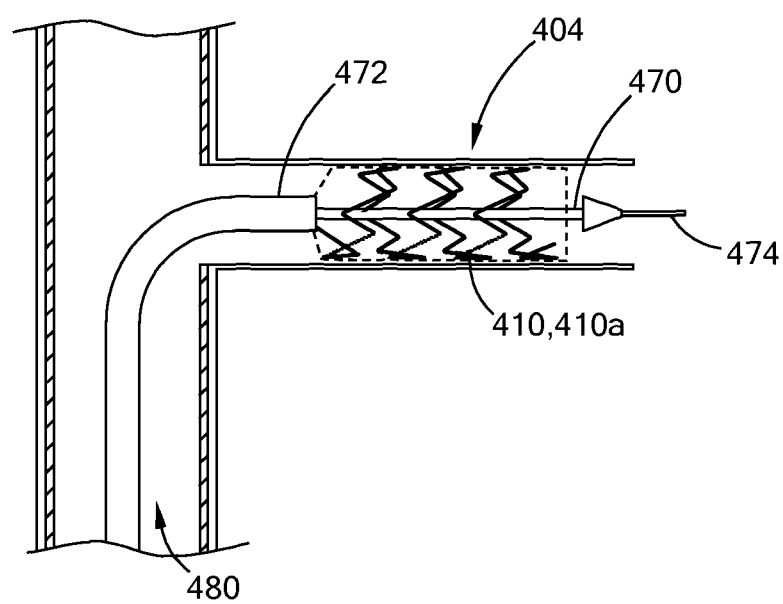

FIG. 4B shows the delivery device 480 with the prosthesis 404 in a partially-deployed state. The tubular sheath 472 has been retracted sufficiently to allow the self-expanding distal portion 410a of the stent body 410 and attached graft material 416 to expand. The balloon-expandable portion 410b of the stent body 410 remains undeployed.

Figure 4C:
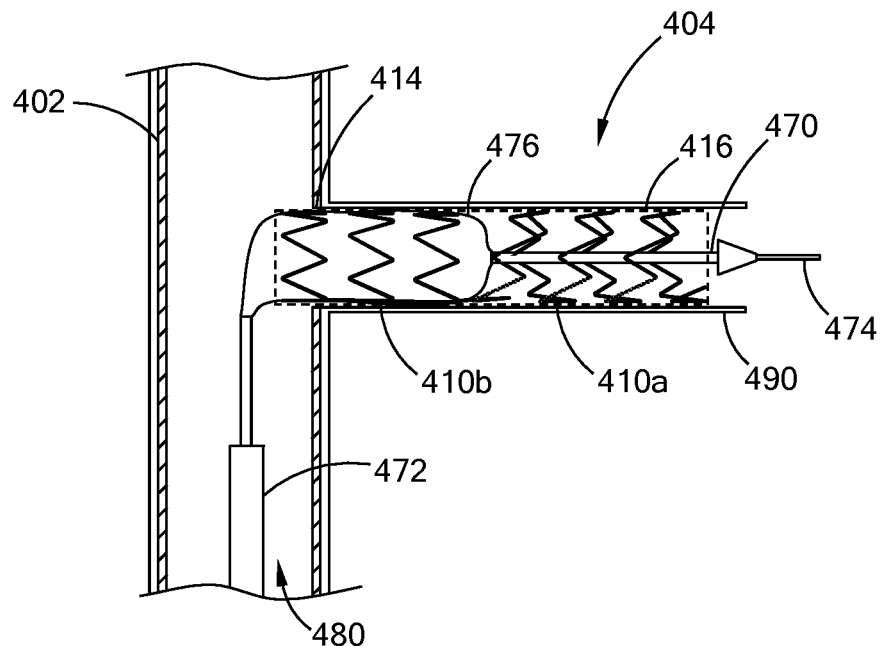

FIG. 4C shows the tubular sheath 472 fully retracted past the proximal portion 410b of the stent body 410 and the introduction of pressurized fluid into the balloon 476 via a balloon inflation lumen, causing the balloon 476 to inflate. As a result, the balloon-expandable proximal portion 110b of the stent body and attached graft material 416 radially expand so that the side branch prosthesis 404 can fully deploy within the branch vessel 490. After radial expansion of the proximal portion 110b, the balloon 476 may be deflated.

Figure 4D:
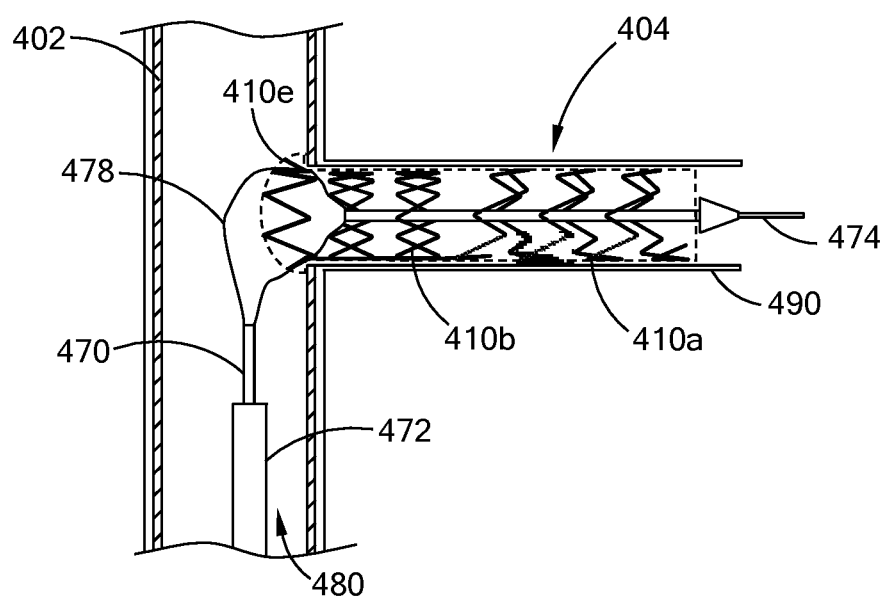

In FIG. 4D, a second balloon 478 is inflated via a second balloon inflation lumen, causing a flareable end portion 410e of the stent body 410 to flare radially outwards, securing the side branch prosthesis 404 to the main vessel prosthesis 402 at the fenestration 414. The graft material 416 of the branch vessel prosthesis 404 may form a fluid seal between the main vessel prosthesis 402 and the branch vessel prosthesis 404. At this point, the second balloon 478 may be deflated and the delivery device 480 and the guidewire 474 may be withdrawn. If needed, a separate balloon catheter may be inserted to further deform the flareable portion 410e to ensure proper engagement between the main vessel prosthesis 402 and the branch vessel prosthesis 404.

Figure 4E:
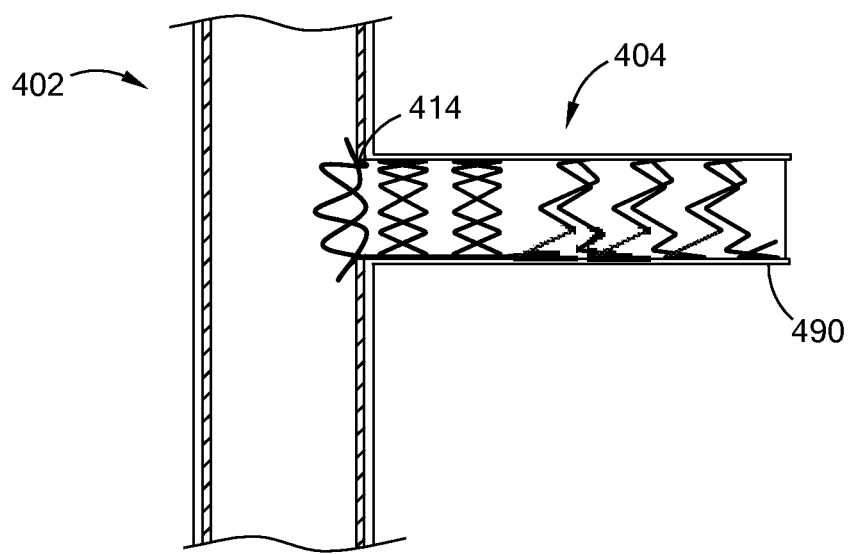

A fully deployed hybrid branch vessel prosthesis 404 is illustrated in FIG. 4E. The hybrid prosthesis 404 may be able to provide higher stiffness near the fenestration and a combination of flexibility and kink-resistance in the branch vessel.

The above-described method provides a true hybrid balloon-expandable/self-expanding stent made from a monolithic cannula or wire. Employing this technology eliminates the need for any welding or joining of two different metals. The balloon expandable portion may be designed to provide rigidity and radial strength, while the self-expanding portion offers flexibility and kink resistance. The technology eliminates the need to reinforce a bridge stent with another device, a feature that may help to drive down the cost of surgery, and it enables deployment in areas with small seal zones, as the balloon-expandable portion of the device can be flared.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein.

Furthermore, the advantages described above are not necessarily the only advantages of the invention, and it is not necessarily expected that all of the described advantages will be achieved with every embodiment of the invention.

The invention claimed is:

1. A method of making a hybrid prosthesis, the method comprising:
  loading a proximal portion of a stent body comprising a shape memory alloy into a first hollow mandrel, the shape memory alloy having values of $A_s$ and $A_f$ below body temperature;
  loading a distal portion of the stent body comprising the shape memory alloy over a second hollow mandrel, the second hollow mandrel comprising one or more throughholes in a wall thereof for passage of a cooling fluid;

heating the proximal portion of the stent body to a temperature in the range of from about 300° C. to about 550° C.;

exposing the distal portion of the stent body to a cooling fluid during the heating; and increasing the values of $A_s$ and $A_f$ in the proximal portion of the stent body to greater than body temperature while the values of $A_s$ and $A_f$ in the distal portion of the stent body remain below body temperature, thereby forming a hybrid prosthesis including a balloon expandable proximal portion and a self-expanding distal portion.

2. The method of claim 1, wherein, prior to loading the proximal portion of the stent body into the first hollow mandrel, the stent body is partially compressed.

3. The method of claim 1, wherein the first hollow mandrel comprises an inner diameter larger than an outer diameter of a compressed medical balloon on a balloon catheter.

4. The method of claim 1, wherein the first hollow mandrel includes a tapered portion at a distal end thereof, a remaining portion of the first hollow mandrel comprising an untapered portion having a substantially constant diameter along a length of the remaining portion, wherein the tapered distal portion increases from the constant diameter to a larger diameter in a direction of the second hollow mandrel.

5. The method of claim 4, wherein the second hollow mandrel has an outer diameter larger than an inner diameter of the first hollow mandrel.

\* \* \* \* \*